United States Patent
Tosaya et al.

(10) Patent No.: US 8,083,707 B2
(45) Date of Patent: Dec. 27, 2011

(54) NON-CONTACT DAMAGE-FREE ULTRASONIC CLEANING OF IMPLANTED OR NATURAL STRUCTURES HAVING MOVING PARTS AND LOCATED IN A LIVING BODY

(76) Inventors: Carol A. Tosaya, Los Altos, CA (US); John W. Sliwa, Jr., Los Altos, CA (US)

( * ) Notice: Subject to any disclaimer, the term of this patent is extended or adjusted under 35 U.S.C. 154(b) by 1630 days.

(21) Appl. No.: 10/826,232

(22) Filed: Apr. 16, 2004

(65) Prior Publication Data

US 2004/0230117 A1 Nov. 18, 2004

Related U.S. Application Data

(60) Provisional application No. 60/463,918, filed on Apr. 17, 2003.

(51) Int. Cl.
*A61B 17/20* (2006.01)
(52) U.S. Cl. .............................................. 604/22; 604/20
(58) Field of Classification Search .................. 604/22, 604/20; 600/439; 606/127, 128
See application file for complete search history.

(56) References Cited

U.S. PATENT DOCUMENTS

| | | | | |
|---|---|---|---|---|
| 3,433,226 A * | 3/1969 | Boyd | ............................. | 606/159 |
| 4,870,953 A * | 10/1989 | DonMicheal et al. | ......... | 606/128 |
| 5,713,831 A * | 2/1998 | Olsson | ................................ | 601/2 |
| 5,725,494 A * | 3/1998 | Brisken | ............................ | 604/22 |
| 5,728,062 A | 3/1998 | Brisken | | |
| 5,853,005 A * | 12/1998 | Scanlon | ......................... | 600/459 |
| 5,931,805 A | 8/1999 | Brisken | | |
| 6,210,393 B1 | 4/2001 | Brisken | | |
| 6,221,038 B1 | 4/2001 | Brisken | | |
| 6,228,046 B1 | 5/2001 | Brisken | | |
| 6,361,554 B1 | 3/2002 | Brisken | | |
| 6,387,116 B1 | 5/2002 | McKenzie et al. | | |
| 6,494,874 B1 | 12/2002 | Brisken | | |
| 6,503,243 B1 | 1/2003 | Brisken | | |
| 6,635,017 B1 * | 10/2003 | Moehring et al. | ............. | 600/439 |
| 7,335,169 B2 * | 2/2008 | Thompson et al. | ................ | 601/2 |
| 2001/0039383 A1 * | 11/2001 | Mohler | ........................ | 600/485 |
| 2002/0177843 A1 * | 11/2002 | Anderson et al. | .................. | 606/1 |
| 2003/0009153 A1 * | 1/2003 | Brisken et al. | ............. | 604/890.1 |
| 2003/0171803 A1 * | 9/2003 | Shimon | ......................... | 623/1.24 |
| 2004/0024347 A1 * | 2/2004 | Wilson et al. | ................... | 604/22 |

* cited by examiner

*Primary Examiner* — Kevin C Sirmons
*Assistant Examiner* — Brandy C Scott

(57) ABSTRACT

Ultrasonic, sonic or vibratory energy, delivered non-invasively, minimally invasively or invasively (e.g. surgically), is utilized to provide direct cleaning action at or to the location of the implanted device such as a prosthetic heart valve with undesirable deposits of at least some amount thereon or therein. Such ultra-sound energy may be aided by the use of a drug in association or cooperation with the acoustic irradiation. The "cleaning" acoustic energy may optionally be delivered under the guidance of an imaging modality and may be delivered in a timed or gated manner such that the valve occluders or leaflets are in a preferred position (assuming they are functioning) during exposures.

13 Claims, 1 Drawing Sheet

NON-CONTACT DAMAGE-FREE ULTRASONIC CLEANING OF IMPLANTED OR NATURAL STRUCTURES HAVING MOVING PARTS AND LOCATED IN A LIVING BODY

CROSS-REFERENCE TO RELATED APPLICATION

The present application claims priority from provisional application Ser. No. 60/463,918, filed Apr. 17, 2003.

TECHNICAL FIELD

The present application is directed generally to prosthetic heart valves, and, more particularly, to cleaning such heart valves, preferably in situ, with acoustic energy.

BACKGROUND ART

Background Discussion

Prosthetic heart valves are probably one of the most well-known implanted medical devices and are installed in an ailing human heart for the purpose of correcting cardiac valvular dysfunctions of various types. Such valves are made either of artificial biocompatible engineering materials, such as pyrolytic carbon, titanium, and silicone, or are fashioned out of donor tissues or actual valves or other tissues sourced from pigs, cattle or human donors.

Particularly for cardiac valves made of such artificial engineering materials, experience has shown that over time, even with the administration of anti-clotting, anti-coagulant or anti-platelet drug treatments, that undesirable buildups of clot, fat, calcium or other undesirable cellular or debris deposits can grow on various valve surfaces and valve pivoting-joints, thereby interfering with valve operation. In extreme cases, the moving occluder portions of such valves can become physically stuck, so the valve is frozen in a random open position. In less severe cases, deposits interfere with the proper seating of the moving occluders, thereby causing leaks and flow irregularities, such as turbulent jets. Such flow affects can encourage more such deposits and/or damage to the blood itself. They also cause functional cardiac problems. Furthermore, such deposits may achieve a finite size, then detach from the valve and cause a downstream clot or stroke elsewhere.

It is also known that even for prosthetic heart valves made from animal or human tissues, that children, in particular, exhibit excessive calcium deposits on such tissue-based valves due to children's unique body processes supporting their growth and maturation. It is also known that calcium deposits may take place inside of valve and other moving tissues, eventually contributing to their stiffening, tearing or stenosis. Expressly included in the scope herein are such buried, interior or interfacial deposits that can possibly cause valve leaflets to fuse together, tear or lose required elasticity.

A general answer to many of these problems, particularly the clotting-based problems, has been to administer a variety of anti-clotting, anticoagulant or anti-platelet drugs. Such clotting-factor inhibiting drugs include warfarin (Coumadin®). Such thrombin inhibitors include heparin or lepirudin (Refludan®). Such anti-platelet drugs include aspirin, ticlopidine (Ticlid®), clopidogrel (Plavix®), tirofiban (Aggrastat®) and eptifibatide (Integrilin®). Some of these medications are administered for years after the implant surgery, if not permanently thereafter. In general, there are some undesirable side-effects to taking many of these drugs, the most important of which are that (a) one's propensity to bleed is enhanced, and (b) in some situations, bleeding can be initiated, particularly in the brain, by such drugs, even without a provoking injury. Thus, major effort has gone into getting the exact bodily concentration of such drugs correct on an ongoing basis. If properly practiced, such drug administration greatly reduces valve deposits, particularly of the clotting type, but does not eliminate such deposits completely. Another answer to these problems has been the avoidance of using engineered material valves in children in favor of bioprosthetic valves made of real tissues. Again, this helps greatly but does not totally eliminate deposition problems.

What would be highly desirable is a device or method for cleaning such deposits, preferably in a damage-free non-contact manner, at least from cardiac implants such as prosthetic valves, in cases wherein the drugs mentioned above have not worked sufficiently to avoid such depositions or could not be used for medical reasons. It would further be attractive if such a device or method could allow for a reduction or even elimination of the use of such anti-clotting (or thrombolytic clot-dissolving) drugs and their undesirable side-effects and lifestyle limitations. For example, using such a device or method, one could avoid the drugs altogether or could take a patient off such drugs for a prolonged period to allow for an unrelated surgery and avoidance of massive bleeding related to that unrelated surgery. So, the present inventors foresee the use of the inventive device and method at least once if not several times on a given patient. Ideally, the device and method can be practiced in noninvasive, semi-invasive, and invasive situations, thus allowing its use in routine maintenance as well as during surgery. Such use could be after cardiac function has been impacted or might be on a maintenance basis before such function is impacted. In all cases, at least some existing deposit would be removed or rendered removable by the body or with the help of an administered drug.

Of particular use would be a device or method which can do so for the moving parts of devices such as heart valve leaflets and can likewise clean other nonmoving parts of actuating implants which would be easily damaged if directly contacted, the damage inviting further deposits. Cleaning the nonmoving parts of such actuating (having moving parts) implants means doing so in the presence of a nearby moving part. Thus, an additional object of the invention is the provision of a non-contact or gentle-contact cleaning method that can clean such implant parts without damaging the moving parts and without damaging the cleaning device itself.

It will be noted from the title that the present inventors include certain deposits on natural body structures also within the scope of the present invention. In particular, the present inventors are not familiar with any art which involves the acoustic removal of undesirable depositions on natural valves, whether they be in the heart or in the lumens such as in the venous or lymphatic system of the legs, for example. There is much art, however, regarding acoustically cleaning lumens that have no moving parts in the sense that valves have moving or swinging occluders or leaflets. Thus, the present invention is directed to the cleaning of valves and body members that are supposed to have moving parts, natural or otherwise.

The bulk of the discussion below will focus on implanted-structure cleaning as depositions are, or at least have the potential to be, more prevalent upon or within them.

The present disclosure also teaches methods and devices to acoustically assess the extent of such deposits-particularly on artificial engineered valves made of engineering materials.

These acoustic or ultrasonic-assessment aspects may or may not be used together with the invention's therapeutic aspects.
Prior Art.

The present inventors have found no art relating directly to the use of ultrasound to clean implanted actuating prosthetic devices of undesirable existing deposits or overgrowths in a non-contact manner while thereby causing no damage, scratching, abrasion or permanent deformation to the implant itself. It should be noted that if contacting-cleaning means were used (such as abrasive devices), then they will cause implant surface-damage or scratching, which will surely invite further such deposits. As mentioned earlier, the present inventors also have not found any teaching regarding acoustically cleaning natural valves normally having natural actuation motions in the cardiac, lymphatic or arterial systems.

Pharmasonics, Inc. has focused several patents on treating vascular tissues prone to hyperplasia or restenosis after a vascular procedure is performed. These patents are directed to preventative procedures and do not deal with deposits that have already taken place nor with deposits on or in actuatable implants or body members. In some cases, there is a lumen stent put in place, which is at least contributing to the restenosis process that they attempt to treat with their inventive therapy. In all cases, their approaches primarily involve treating the distressed tissues adjacent the stent such that those tissues do not overgrow the stent interior diameter, causing flow-blockage. There are no actuating or moving parts whose actuation would be interfered with by the deposits. Our definition of a moving or actuating member covers any implant, natural member or organ wherein any solid or semisolid material (like tissue or metal, for instance) is expected to actuate at least once. Thus, venous, lymphatic and cardiac valves of natural and implanted types are covered. We include in our scope actuation being the one-time or occasional alteration, maintenance, adjustment or servicing of an implant that may be fouled by such deposits. A perfect example of this is, for example, a pacemaker lead that has been fouled by tissue or deposit overgrowth such that it needs to be cleaned so that it can function properly or be exchanged for a new one. There the actuation is a one-time plugging-in (and out) of an electrical lead connector. Two last examples of actuation are the normal cyclic motion of various bodily organs due to perfusion (e.g., heart, kidney, liver) and the actuation of muscles and tendons. In both of those cases, known deposits can interfere with the normal distension or extension of such members and would benefit from the therapy of this invention.

U.S. Pat. No. 6,361,554 to Brisken (and assigned to Pharmasonics) and U.S. Pat. No. 6,387,116 to McKenzie (and assigned to Pharmasonics) are the nearest to being relevant to the discussion here and will be discussed below. However, neither patent alone nor in combination with the other, leads one to the present invention herein. Other patents reviewed but not considered at all relevant include U.S. Pat. Nos. 5,725,494; 5,728,062; 5,931,805; 6,210,393; 6,221,038; 6,228,046; 6,494,874; and 6,503,243, all to Brisken (and assigned to Pharmasonics).

U.S. Pat. No. 6,361,554 to Brisken (the '554 patent) is entitled "Methods and Apparatus for the Subcutaneous Delivery of Acoustic Vibrations". What this patent teaches is a preventative therapy to avoid undesired stent depositions, not the removal of prior depositions nor the removal of depositions interfering with or potentially interfering with the actuation or distension of an implant or body member. Brisken utilizes the sonically-driven stent resonation to indirectly treat the tissue adjacent the stent and prevent it from later forming overgrowths onto or into the stent. More specifically, he teaches that acoustic excitations are delivered from outside the body, that the stent is smaller than his illuminating beamwidth, and that the stent is specifically pre-designed or modified to have a characteristic resonant frequency. Furthermore, the characteristic pre-chosen resonant frequency is utilized in a manner such that the resonant stent causes acoustic energy to be preferentially redeposited at the diseased interfaces between the stent and the adjacent tissues by his process of re-radiation in the form of reradiated (from the driven stent) vibrations or heat. Note that multiple treatments are suggested and that using a semi-invasive catheter for such treatments is taught to be avoided. The reader will appreciate that a stent, once placed, is a nonactuating device not subject to brittle fracture. The beamwidth being so much larger than the stent allows for easy aiming. Recommended implants for the preventative therapy delivered by the '554 patent focus on vascular stents, grafts and valves widely familiar to the vascular surgeon. Note that because the '554 patent utilizes externally applied ultrasound, that ultrasound cannot directly illuminate the stent or implant interior, thus the need for an indirect approach. So direct treatment of deposits is not taught-only indirect treatment-and only noninvasive indirect treatment. By direct treatment we mean that the ultrasound energy performs its function directly on a deposit. The above prior art performs only noninvasive indirect therapy wherein existing deposits are not directly targeted, and furthermore are taught to be avoided by advance use of that invention before such deposits exist.

Contrary to the '554 patent, the invention herein has several fundamental differences including the following: (1) deposit materials that have already deposited or formed are themselves treated, (2) the deposits are primarily treated directly, not indirectly, (3) re-radiation is not primarily depended upon to provide an indirectly delivered or preferentially focused therapy, (4) the implant is not required to be modified in design to achieve a particular resonance, (5) it is recognized that any resonant property of the implant, if present, will vary as a function of the deposit burden attached thereto, (6) the acoustic signature of a clean implant is optionally utilized to deduce the presence and extent of such deposits and the progress of their removal, (7) it is recognized that any deformable implant (such as a stent) will have its native resonant frequency(s) modified by the exact amount of deformation and by the loading by adjacent tissues, and (8) it is recognized that some implants are subject to brittle fracture and can be broken by such driven resonances, particularly implants made of ceramics or glasses which are not acoustically lossy and are brittle. Furthermore, the '554 patent does not teach what acoustics are reradiated, i.e., whether they are harmonics of the driving frequency or are solely the primary driving frequency. The present inventors specifically discuss the management of such harmonics if they are allowed to be present.

U.S. Pat. No. 6,387,116 to McKenzie (the '116 patent) entitled "Methods and Kits for the Inhibition of Hyperplasia in Vascular Fistulas and Grafts" is somewhat similar to the above, except that it typically involves only natural tissue structures therein whose potential hyperplasia is to be avoided. Note that there is no mention of any resonant attribute of an artificial implant, stent or graft nor any mention of using the acoustics themselves to clean up prior deposits. New elements relative to the '554 patent are the use of a drug if desired, the avoidance of cavitation, and the avoidance of temperature rises of more than 2 degrees Centigrade. Since there is virtually no discussion of any implant's acoustic properties nor the cleaning of prior deposits on any implant, this patent is thus, after inspection, regarded as irrelevant. It is also preventative in nature like the '554 patent.

Thus, there remains a need for a mechanism for removing undesirable deposits from an implanted device, such as a prosthetic heart valve, having at least one moving or movable part. This need also extends to such deposits in or on a natural bodily member or organ having a naturally moving, distending or actuating part or portion. The need also extends to one-time actuation required to maintain or service existing implants, the actuation being a required movement of at least a portion of the implant or its connection means. Thus, the replacement of a fouled pacemaker lead is included within the scope of the present invention because the lead and its connector must be moved (removed and exchanged) relative to the pacemaker body itself.

DISCLOSURE OF INVENTION

In accordance with the present invention, ultrasonic, sonic or vibratory energy, delivered non-invasively, minimally invasively or invasively (e.g., surgically), is utilized to preferably provide direct cleaning action at or to the location of an implanted artificial or bioprosthetic device, such as a prosthetic heart valve, or a natural bodily member or organ with a naturally moving, actuating or distending part or portion with undesirable deposits of at least some amount thereon or therein. Such ultrasound energy may be aided by the use of a drug in association or cooperation with the acoustic irradiation. If a drug is used, the ultrasound may enhance the performance of that drug via its acoustic and/or thermal attributes. Alternatively, or in addition, the drug may make it easier to achieve deposit removal by destabilizing or softening such deposits. Such a drug might be given at least one of before, during or after the acoustic therapy.

Specifically in accordance with the present invention, apparatus is provided that is capable of the non-contact or damage-free removal or erosion of undesirable deposits situated: (a) on or in an implanted artificial or bioprosthetic device having at least one moving or movable, actuatable or distendable part or portion ("moving or movable" hereinafter), or (b) on or in a natural bodily member or organ having a naturally moving or movable part or portion. The deposits to be removed or eroded interfere or potentially interfere with at least one of (a) any designed function of the implanted device, (b) any natural function of the natural bodily member or organ, or (c) any circulatory system process necessary for normal healthy living. The apparatus comprises:
  an acoustic emitter capable of emitting acoustic energy;
  a means for exciting the acoustic emitter to emit acoustic energy;
  a means for acoustically coupling the acoustic energy into the deposits directly or indirectly;
  a means for operating the emitter(s) to at least partially remove or otherwise erode the deposits; and
  optionally, an administered drug to aid the removal or erosion process, to prevent or slow further such deposits, or to treat a side-effect of treatment with the emitter.

Further in accordance with the present invention, an acoustic method capable of the non-contact removal or erosion of such undesirable deposits is provided. The method comprises:
  providing the acoustic emitter;
  exciting the acoustic emitter to emit the acoustic energy;
  acoustically coupling the energy into the deposits, directly or indirectly, to at least partially remove or otherwise erode the deposits;
  either passing the at least partially removed deposits or otherwise eroded deposits into the body or physically removing the at least partially removed deposits or otherwise eroded deposits by a collection, trapping or immobilization means; and
  optionally administering a drug to aid the removal or immobilization.

Still further in accordance with the present invention, a method is provided for assessing the state of fouling by undesirable deposits of an implant or of a natural valve in a living body, the implant or valve having at least one moving or movable part. The method comprises:
  obtaining, in any manner, an acoustic signature of the operation of the implant or valve at least under unfouled conditions inside or outside a living body;
  obtaining, in any manner, using passive reception or pulse-echo active probing, an acoustic signature of the implant or valve thought to possibly have fouling thereon or therein;
  the possibly-fouled signature containing at least one of: (1) naturally generated acoustic features known to be caused by fouling, and (2) artificially excited features known to be excited upon the presence of fouling;
  comparing the fingerprints looking for fouling features that have newly been incorporated into the signature; and
  concluding that newly added features which match known fouling features indicate fouling.

The "cleaning" acoustic energy may optionally be delivered under the coordinated or real-time guidance of an imaging modality and may be delivered in a timed or gated manner such that the valve occluders or leaflets are in a preferred position (assuming they are functioning) during exposures. For example, if the cleaning ultrasound is delivered via a catheter, then it might be delivered to a valve from inside or outside the heart. If it is delivered via a transesophageal transducer, then it would be delivered from the esophagus. If it is delivered surgically, then it might be delivered upon a surface of the exposed beating heart or onto a lumen connecting to the valve in question. A combined ultrasound imaging probe and ultrasonic cleaning probe containing one or more transducers could be employed, for example. It is to be emphasized that the invention may or may not involve bodily resonating the implant, or a portion thereof, itself, and in all cases at least some direct cleaning action is delivered which does not require such implant resonating; the deposit is directly bathed in emissions and is itself broken down or acted upon directly. The implant might be an artificial prosthetic heart valve or a combination valve/stent in a venous lumen, for example. In all cases, a pre-existing deposit is operated upon. The scope of the invention includes any implanted artificial or bioprosthetic device, natural bodily member or organ having a moving or movable part or portion that is subject to undesirable depositions on or in it, which could, or do, negatively impact the patient directly or indirectly. This would include the cleaning or dissolution of depositions, which would only harm the patient if they were to break free and passage into the bloodstream. Thus, it would include removing deposits from the nonmoving parts of heart valves as well, such a heart valve requiring a non-contact damage-free method of cleaning of any or all of its parts.

The present inventors further teach, particularly for fragile non-deformable implants such as engineered artificial heart valves, that one may utilize acoustic spectral characteristics of clean vs. dirty implants to deduce something about the extent of such deposits or the extent of their removal. The avoidance of delivering acoustic energies that could fracture such brittle implants is also taught.

Finally, the present inventors teach that the cleaning acoustics may be directed at a portion of the implant, member or organ such that the acoustic intensity is maximized at desired locations or such that other fragile portions of the implant are avoided by the cleaning processes.

BEST MODES FOR CARRYING OUT THE INVENTION

Figure 1:
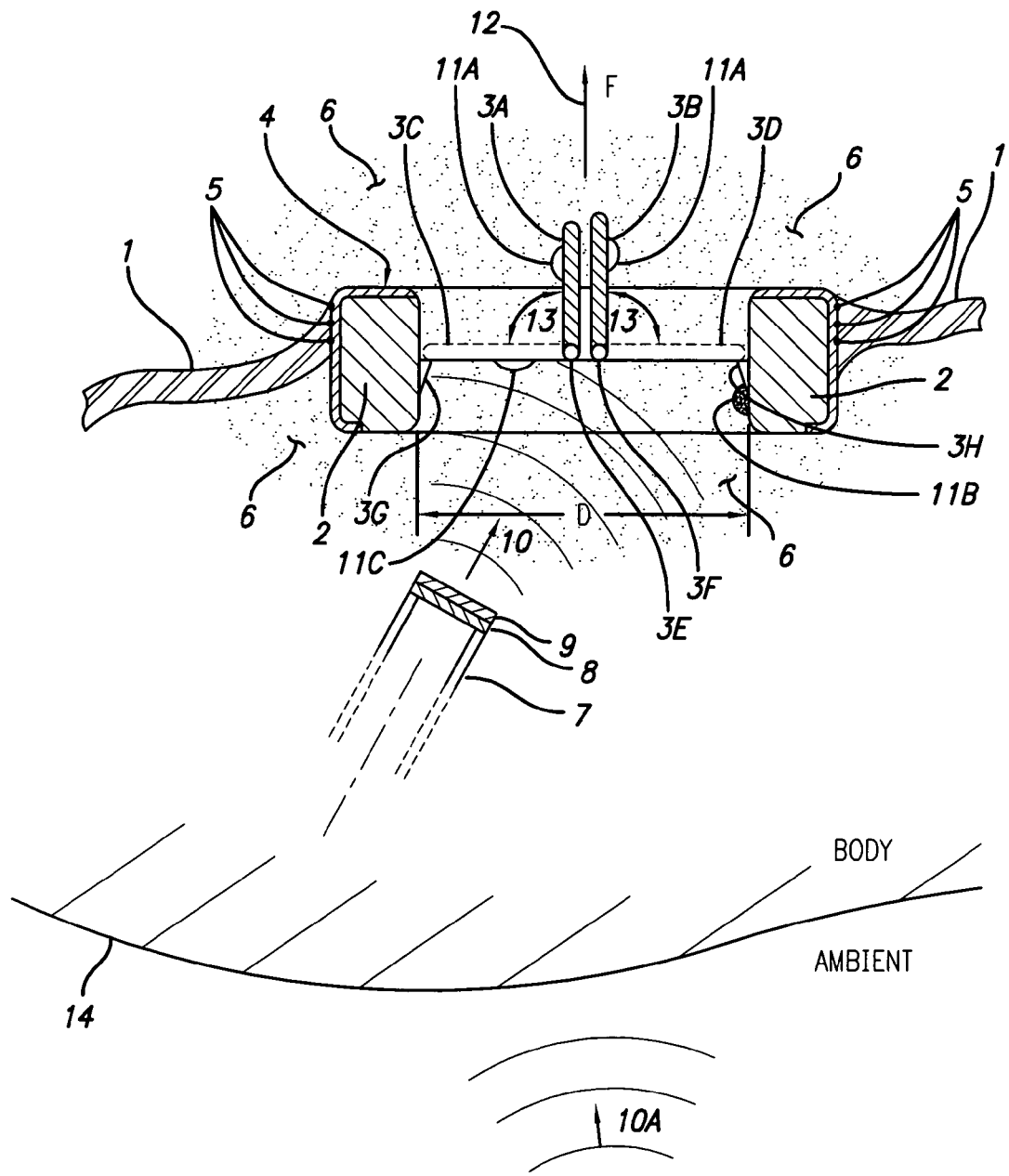
FIG. 1, the sole Figure, schematically depicts a (non-tissue) prosthetic heart valve mounted in a patient's heart, the valve having undesirable deposits thereon and therein, wherein ultrasound waves are shown directed toward the deposits from an invasive (in this example) therapy transducer of the present invention.

Moving directly now to the Figure, there is shown (not to scale) an artificial prosthetic heart valve 2 mounted in cardiac tissue 1 defining a chamber of the heart. In fact, item 2 is the known typical annular valve body of such a valve. Typically, body 2 is made of pyrolytic carbon or titanium. Typically, the valve 2 will have one or more swinging leaflets or occluders 3A and 3B as shown. Note that in the Figure, normal blood flow F is upwards in the direction of flow arrow 12. Valve 2 acts as a check valve preventing downwards flow by closing its leaflets 3A and 3B to the respective closed and seated phantom positions 3C and 3D. The leaflets swing as indicated by arrows 13. Also typically, leaflets 3A and 3B will swing upon hinged pivots of the type 3E and 3F. The axis of such pivoting is normal to the plane of the drawing. Typically, valves will have a fabric covering 4, which allows the use of sutures 5 to attach the valve 2 to the cardiac tissue or annulus 1. Blood 6 is shown as being present on both sides of the valve 2, with its desired flow 12 upwards for the sake of illustration. Finally, as is known in the art of valve construction, the moving leaflets 3A and 3B seat themselves in their phantom closed positions 3C and 3D upon a sealing valve seat seen in section as rim 3G and 3H.

While the majority of the description herein is directed to implanted artificial or bioprosthetic devices having at least one moving or movable part or portion, it will be readily appreciated by those skilled in this art that the same teachings may be applied to a natural bodily member or organ having a naturally moving or movable part or portion. In all cases, the deposits either interfere or potentially interfere with at least one of (a) any designed function (or any required maintenance) of the implanted device, (b) any natural function of the natural bodily member or organ, or (c) any circulatory system process necessary for normal healthy living.

The valve 2 thus may be an artificial, bioprosthetic, or natural valve, located anywhere in the body and having at least one moving part, referred to herein as a leaflet or an occluder 3A, 3B. The valve 2 may be of any type supportive of a patient's cardiac, lymphatic or arterial systems. The leaflet or occluder 3A, 3B, if the valve 2 is artificial or bioprosthetic, may comprise a biocompatible engineering material such as pyrolytic carbon. Such biocompatible engineering materials are well-known. Alternatively, the leaflet or occluder 3A, 3B may comprise a tissue material of any type, whether natural or bioprosthetic. The tissue may be, at least in part, donor human tissue, donor animal tissue, lab-grown tissue or artificial tissue.

The leaflet or occluder 3A, 3B may be a part of the patient's own natural valve, anywhere in the body. Examples of such natural valves include cardiac valves, venous valves, and lymphatic valves. We emphasize occluders as they are commonly fouled but we include in the scope any other connecting tissues or muscles which, if fouled by deposits, will cause a functional valve problem.

Referring back to FIG. 1, it will be noted that there are undesirable deposits 11A, 11B, 11C upon the valve in various places. Deposits 11A are on the leaflets themselves. Deposit 11B is inside the annulus 2. Deposit 11C is in the dangerously nearby region of the valve seat 3G, 3H. Those skilled in the art of valves and valve deposits know that such deposits can also take place in numerous other positions or inside/outside surfaces (not shown), including within the pivot or hinge region(s) 3E, 3F, on the leaflet edges, or directly on the valve-seat sealing surfaces etc. It is not the point here to teach such details of historical deposit distributions.

At least some of the deposits are on or in at least one of the moving, movable or nonmoving parts of the implant, member or organ and presents a potential or existing problem. For example, the deposits may be on the leaflet or occluder, which moves, or on the seating or sealing edge or face against which the leaflet or occluder seals. Or, at least some of the deposits may interfere with the proper moving of a moving part of the implant or interfere with a moving part or medical device arranged or designed to be passed through, passed into, mated to or threaded into the implant, such as a hinge, pivot or flexural area of the valve.

The presence of the deposits may likely ease or encourage the formation of additional deposits as is known from clinical experience. The deposits may interfere with the designed or natural function of the implant, member or organ, thereby interfering in the desired hydrodynamic operation of a natural or implanted valve supporting the heart, the lymphatic system or the arterial system. Thus, the deposits may interfere with normal blood flow trajectories, normal hemodynamics or normal cardiac capacity. The removal of deposits as taught herein may prevent a potential stroke or any cardiac dysfunction or degraded function.

Specifically included in the scope of "deposits" is pannus, which is an occasional lateral tissue overgrowth (not shown) onto the valve surface or valve throat. Although pannus is technically not a deposit, it is still a cleanable (or killable) tissue material that interferes with valve operation. Also included in the scope of "deposits" are blood constituents, whether clotted or not, calcium, fatty deposits, bodily organic debris, and bacteria. Specific examples of such deposits include, but are not limited to, at least one of (a) surface-deposited, calcium-containing material, (b) calcium-based deposits inside tissues or in tissue interfaces, (c) calcium-based deposits inside implant materials or in an interface including at least one implant material, (d) fatty deposits on surfaces or inside tissues or engineering materials, (e) organic debris on surfaces or inside tissues or engineering materials, (f) plaque-like deposits, and (g) any deposit which contributes to stenosis or a loss of elasticity of a moving or movable tissue or implant component.

It will be noted that the valve 2 is depicted oversize in section within a patient's body having a skin surface 14. Outside the skin surface 14, there is the possibility of applying a noninvasive acoustic treatment and/or an invasive treatment can be applied from inside the body. Details of the heart are not shown in the Figure, as they are not necessary to understand the invention. Given the choice between noninvasive (no incisions), semi-invasive (small incisions), minimally invasive (tiny localized incisions or punctures) and invasive (large incisions) acoustic energy delivery, any one of the heart valves can be acoustically illuminated from at least one direction or angle to achieve the inventors' purpose here.

We emphasize here that the therapy of the invention, if invasive to any degree, may be done along with other surgery already being done and thus our therapy is not the root cause of an invasive procedure. This makes the invention a concomitant procedure in those cases. Such situations are a common surgical occurrence and are quite common in heart surgery, for example.

By way of invasive or semi-invasive energy delivery, a catheter or other ultrasound probe 7 is shown, directed toward the valve 2 in FIG. 1. Such a probe could be delivered, for example, through the femoral artery, carotid artery or through a laparoscope through the chest. Acoustic device 7 is shown as having an acoustic emitter 8 and an acoustic matching layer 9. Acoustic cleaning waves 10 are shown directed toward the valve 2 for purposes of cleaning or removing deposits of the type 11A, 11B, 11C or pannus (not shown). Those familiar with the acoustic art know that piezoelectric, ferroelectric, electrostrictive, magnetostrictive, or thermoacoustic transducers can be fabricated to deliver directed acoustics in the manner shown. Optoacoustic or laser-based acoustics-producing catheters may also be employed.

As an example, transducer 8, 9 could be a piezoceramic (PZT or lead-zirconate-titanate) transducer operating at 1 megahertz in single-pulse, multipulse or continuous wave fashion.

The acoustic emitter 8, as an alternative option, may be temporarily or permanently integrated into the patient's body or into the implant itself, and may be automatically operated without constant patient or doctor manipulation. Alternatively, the acoustic emitter 8 may be integrated or co-mounted with an imaging device, such as an ultrasound transducer, an infrared camera or an imaging scope of any type used during therapy. Thus, an independent imaging device may be employed, such as to guide or plan a treatment. Examples of such independent imaging devices include, but are not limited to, ultrasound imaging, fluoroscopy, MRI (Magnetic Resonance Imaging), CAT (Computed Axial Tomography) scan, PET (Positron Emission Tomography) or videoscope with a waterpath.

The transducer 8, 9, in the invasive case shown, might be moved in close proximity to the valve 2 (as shown) such that the delivered acoustics are mainly directed to areas of the valve needing cleaning. Thus, the transducer might be focused or unfocused, depending on the working distance desired. Focusing would likely be done for small working distances, which allow for minimal (total) acoustic power to be used to get the job done. The present inventors anticipate the use of protective devices (not shown) such that the cleaning transducer is not mechanically caught up in the moving leaflets 3A, 3B. Thus, the implant, member or organ may be at least temporarily immobilized; such immobilization may be done by the juxtaposition or insertion of a soft or compliant protective member than mechanically blocks the motion, such as an inflatable balloon or other pressurized member, inflated by at least one of a liquid or a gas. As an example, one could envelope the probe 7 tip in a saline filled balloon (not shown) such that if the balloon did hit a moving leaflet, there would be no mechanical damage to the valve by the transducer nor any damage to the transducer. It should be emphasized that preferably a non-contact scheme is employed, at least in the sense that no portions of the therapy device 7 which could interfere with or damage the implant surfaces come in contact with such surfaces. Recall that even minor surface scratches invite more deposition activity. Thus, either no portion of the emitter means 8, 9 contacts the implant, member or organ or any portion of the emitter means 8, 9 that does contact the implant, member or organ comprises a compliant or deformable protection-affording material.

Outside the patient's body 14 is shown alternative acoustic delivery of therapy waves 10A. This is to emphasize that the acoustic energy may be delivered from anywhere on (coupled-to in any manner) or in the body in any noninvasive, minimally-invasive or invasive manner. The delivery location will probably be determined at least in part by whether the therapy is of a scheduled maintenance sort or is being delivered together with a related or unrelated surgery, possibly to fix serious functional problems.

Acoustic, sonic or vibratory energy 10 or 10A preferably acts directly upon deposits 11A, 11B, 11C that are typically enveloped by surrounding blood 6 (or other liquid or tissue path between the emitter and the deposits) capable of transmitting such acoustics directly into the deposits. In this manner, it is not necessary to pre-design the implant such that it can be resonated at a particular frequency. The acoustic energy may act upon at least a portion of the deposits, possibly in cooperation with one or more drugs, to break-up, breakdown, dissolve, de-amalgamate, erode or otherwise attack the deposits. For example, the acoustic energy may aid in the permeation of the deposits by such drug(s) or by a natural anti-clotting blood constituent or both. Such action may or may not include significant cavitation, streaming, erosion or dissolution phenomena in the region of the deposits, depending on the fragility of the implant. Cavitation and streaming will further accelerate these removal/erosive processes. The inventive therapy allows for heating of the deposits using the ultrasound exposure, if that accelerated deposition breakdown (e.g., for fatty layers). It will be noted that many valve parts, such as pyrolytic leaflet occluders, can be safely heated without damage-particularly by higher frequencies (e.g., 7 to 12 MHz) that will not cause resonant damage to the valve itself. In this manner, heating of several tens of degrees Centigrade or more is allowable, and can be thermally quenched quickly by the blood flow. Within the ambit of the present invention is the use of blood additives such as contrast microbubbles to provide cavitation nucleation sites. Such microbubbles would ideally be burst and cavitated only in the direct neighborhood of (or within) the deposits to be removed. Thus cavitation may optionally be aided by the presence of cavitation nuclei or facilitators, such as contrast microbubbles, gas bubbles or surfactants.

The acoustic energy may be coupled into the implant, member or organ by, for example, (a) coupling to a patient's external skin, (b) coupling from within a patient's natural body passage or space, (c) coupling into the surface of a surgically exposed or accessed organ or tissue surface, (d) coupling from a natural body lumen into an organ or implant, or (e) coupling into a cardiac structure or implant from within a cardiac chamber.

Frequencies of acoustic excitation may be in the range of 1 Hz to 100 MHz, preferably in the range of 1 KHz to 10 MHz, and most preferably in the range of 5 KHz to 10 MHz. Acoustic powers may be in the range of milliwatts per square centimeter to kilowatts per square centimeter, preferably in the range of 0.5 watts/cm$^2$ to 5000 watts/cm$^2$, and most preferably in the range of 5 to 500 watts/cm$^2$. The particular acoustic energy selected is chosen for its ability to remove the deposits upon direct radiation by the acoustic energy. The determination of the conditions for such removal is not considered to constitute undue experimentation.

The acoustics may be focused, collimated, weakly focused, or unfocused. Preferably, they will be at least collimated if not somewhat focused to achieve a higher useful power density in the treatment field. The transducer or emitter, if focused, may be mechanically focused and/or electronically focused, beam-formed or steered as by use of a multi-element array technology, which is widely known. Preferably, the useful treatment portion of the beam will be large enough such that precision unaided mechanical scanning of the implant is not required. As an example, a treatment catheter could have a 7 mm diameter with a 7 mm diameter spherically-focused transducer at the tip. The transducer could be weakly focused inwards to a point, for example, at 25 mm distance. In this manner, the transducer can paint large swaths of the implant if it is held at a distance in the range of 5 to 15 mm, for example. The patient may receive one or more treatments or multiple scheduled treatments.

Included within the ambit of the present invention is the choosing of a frequency such that one of these four conditions is met: (a) a frequency employed has a characteristic wavelength on the order of a characteristic dimension of a typical deposit or deposit constituent, thus improving coupling into the deposit, (b) a frequency employed is chosen because it is known to be capable of exciting a resonance or resonance harmonic in an implant portion, (c) a frequency employed is known not to excite a resonance or resonance harmonic in an implant portion, or (d) broadband frequency or scanned frequency is employed in order to gain the benefits of more than a single frequency. The resonant excitation may contribute to indirect delivery of acoustic energy into the deposits and the energy may contribute to the removal or erosion of the deposits. Indirect energy may be deposited upon or into the deposits by first coupling the acoustic emissions into the implant, member or organ and then the acoustic energy in turn being delivered to the deposit(s). Many applications of the invention will involve using frequencies that directly attack deposits but fail to excite implant resonances. Typically, this means frequencies which are chosen to not be equal to a harmonic or base-frequency of an implant resonance-particularly one of the lower harmonics whose amplitude would be expected to be larger than that of a higher harmonic. So, for example, if the implanted valve had a resonant frequency at 100 KHz and it is desired to have only direct deposit attack and no resonant excitement we would choose not to utilize a frequency f, at least not for any significant pulse-length, having a value of, for example, ½f, 1f, 2f, 3f, etc. or 50 KHz, 100 KHz, 200 KHz, 300 KHz etc. Thus, we could likely utilize 1 MHz, for example.

In general, the less intervening tissue that is situated between the therapy transducer and the implant to be cleaned, the higher the frequency can be because intervening tissue losses are not the limiting factor. Thus, in the Figure, emissions 10 could be in the few megahertz and above range, while emissions 10A would preferably be somewhat lower in frequency, e.g., a few megahertz or lower.

In general, one does not want to deliver excessive high power acoustic waves to an artificial implant that has brittle components with resonant frequencies that could be excited by the therapy transducer. It might indeed be possible to deliver enough grossly excessive acoustic power to break pyrolytic carbon leaflets 3A and 3B if that delivery were at a resonant frequency of the leaflet. Thus, it is preferred that the primary mechanism of deposition attack is direct, which does not require the implant itself be maximally and efficiently resonated and merely requires that acoustic energy can arrive at a deposition through blood, through tissue, or through the implant in the form of non-resonant excitations. Also included in the ambit of the present invention is resonance of at least a portion of the implant at an amplitude known to be safe from prior engineering characterization. Such driven resonance or non-resonant vibrations add the indirect deposition attack mode because the deposition is essentially being shaken on a driven moving foundation (the implant). We note specifically that even for an artificial valve having a resonance of its leaflet, say at 100 KHz, that the blood substantially dampens the resonant vibrations. Thus, our intent is to avoid unacceptable resonant vibration amplitudes, and the easiest way to do this is to avoid resonant peaks completely. However, the scope of our invention includes resonating implants wherein the resonant amplitudes are safely below damage thresholds but above those that aid in deposit indirect-attack. Thus, specifically included within the ambit of the invention is the avoidance of known or measured (in-vivo or ex-vivo) resonant frequencies or the use of such resonant frequencies in a manner not exciting damaging resonant amplitudes in the presence of the existing damping. Thus, the acoustic energy may be one of (a) does not appreciably resonate the implant, member or organ at one of its resonant frequencies that could otherwise cause damage to the implant, member or organ, or (b) does appreciably resonate the implant, member or organ at a resonant frequency thereof, but does so at an amplitude below that known to damage the implant, member or organ and the resonance is not employed for indirect deposit-attack, or (c) does appreciably resonate the implant, member or organ but does so below an implant damage threshold but above a deposition-attack threshold.

The optional use of drugs is mentioned above. A variety of drugs may be used, including, but not limited to, thrombolytic therapy drugs (clot dissolvers), including drugs such as alteplase (Activase®), anistreplase (Eminase®), streptokinase (Streptase® or Kabikinase®), urokinase (Abbokinase®), and tissue plasminogen activators referred to as TPAs of various sorts (types of TPA), or an anti-clotting, anti-coagulant or anti-platelet drug such as a clotting factor inhibiting drug include warfarin (Coumadin®), a thrombin inhibitor such as heparin or lepirudin (Refludan®) or an anti-platelet drug such as aspirin, ticlopidine (Ticlid®), clopidogrel (Plavix®), tirofiban (Aggrastat®) and eptifibatide (Integrilin®). The drugs may be employed before, during or after an acoustic exposure in order to aid in removal or erosion of the deposits. The acoustic energy may accelerate or enable action of the drug. The drug(s) may be locally delivered to the deposits, such as via a catheter or working port of a scope or may be systemically delivered.

Alternatively, the ultrasound may act alone without thrombolytic drugs or any other drugs which directly or indirectly assist in deposit removal. One may also choose to administer a drug in association with the inventive acoustic treatments simply to prevent any potential side-effects of the acoustic exposures themselves.

One may characterize an artificial implant before or soon after implantation to understand its acoustic signature in its clean deposition-free condition. This scheme is particularly useful for characterizing leaflet deposits on prosthetic valves because the occluders are mainly liquid-loaded and have only small acoustic losses out their hinges 3E, 3F. Thus, deposits on the leaflets or hinges will noticeably affect the spectral fingerprint of such a valve. The worst deposits, those that mechanically interfere with the leaflet or occluder motion or occluder seating, will have the largest acoustic fingerprint change. By "fingerprint" is meant an acoustic signature that has one or both of the following content: (a) a passively received spectra comprising naturally generated noises coming from the valve or the valve's functioning and (b) actively generated spectra generated using acoustic excitations. Particularly with regard to (a), it is widely know that heart valves can be quite audibly (and inaudibly) noisy and can even be heard by the patient on occasion; thus, efforts go into designing them to be as quiet as possible. So within the scope of the invention is the taking of acoustic fingerprints of such implants, preferably before and after depositions, using sensitive reception-microphones or transducers, such that the acoustic effects of such depositions can be used to deduce fouling or deduce the progress of fouling removal. Those who have used ultrasound imaging realize that it is not always possible to image such deposits until they are quite large. Thus, this additional fingerprinting tool is provided herein which is more sensitive to small depositions, particularly on moving parts. Use of this fingerprint tool does not preclude ultrasound imaging and may even be incorporated into an ultrasound imaging transducer. Consequently, the acoustic emitter may also comprise or be co-mounted, co-packaged or used in association with an acoustic device used to gather an acoustic fingerprint indicative of the extent, location or nature of deposits. Alternatively, the fingerprints may be taken or generated by an acoustic device that is independent of the acoustic emitter.

It should also be emphasized that an implant portion, such as a leaflet 3A, 3B, can be driven not only at a resonant frequency but can also be driven directly or indirectly at one of its higher harmonic frequencies. Specifically included within the scope of the invention are acoustic illuminations for finger-printing that excite harmonics directly (by driving at the harmonic frequency) or indirectly (by driving at the primary frequency) or by driving in a broadband manner. Driving at a resonance or harmonic will maximize the signal to noise ratio, but one must remain below pre-known and pre-characterized critical amplitudes that could cause breakage.

Returning to the description of the invention, it was mentioned that the cleaning of natural (pre-existing non-implanted) valves or of natural tissue overgrowths (pannus) onto artificial valves is included within the teachings herein. A first example of this would be the cleaning of calcium deposits from a bioprosthetic (tissue-based) valve in a child. Such tissue-based replacement valves in children are particularly prone to calcium deposits.

A second example would be the cleaning or necrosing of pannus, which is the lateral overgrowth of the patient's tissues into or onto an artificial prosthetic valve. In this unique case, killing living tissue occurs and this procedure would tend to use the higher specified powers at the higher specified frequencies using a close-in delivery transducer such as 8. This is because it is desired to preferably heat the pannus and kill it. In this example, the acoustic energy has a frequency within a range of 3 to 10 MHz and an acoustic power of several hundred to a few thousand watts/cm$^2$ at the most intense portion of the beam. Although thermal heating may be used to kill pannus, pannus may alternatively be killed by cavitation or a combination of thermal heating and cavitation.

In general, deposits 11A, 11B, 11C will be formed of blood-based thrombus and will be thermally blood-coupled. The point is that a fair amount of acoustic power may be delivered (tens or hundreds of watts/cm$^2$) without appreciably heating the deposits because of the excellent heatsinking situation to the blood and to the underlying implant itself. Obviously, if the underlying implant material is a thermally conductive metal, this is particularly true. This will invite easier acoustic breakdown of the deposit without burning it into an insoluble form. The same benefit extends to calcium deposits whether they be on or within artificial valves, bioprosthetic valves, natural valves or valve tissues. It is also noted that the implant in general will have an acoustic impedance that significantly mismatches that of blood, such that energy delivery into the implant material itself is reduced in favor of delivery into the deposits in the known manner taking account of the therefore-different acoustic reflectivities.

It is expected that it may be preferable to gate the energy delivery in time with the open or closed state of a moving functioning valve. This would be for at least one of three reasons. The first is that it may be easier to illuminate a leaflet-deposit at a particular angle of a moving leaflet. The second reason is that it may be beneficial to use a portion of the implant or moving leaflet to shield some other portion of the heart (or implant) from the acoustics. The third reason is that it may be beneficial to allow cooling or allow for microscopic debris to be carried off with each heartbeat, where the debris is of sufficiently fine size that it can be allowed to pass into the circulatory system safely. Finally, it may also be beneficial to intersperse imaging activity such as ultrasound B-mode or color flow mode imaging. It may also be beneficial to intersperse the previously mentioned acoustic fingerprinting activity to assess deposition removal in real time.

Known to the ultrasonic arts of imaging and tissue therapy are numerous RF-driving means and control-logic to excite such transducers with single pulses, pulse trains, or continuous pulses. Also widely known are acoustic spectroscopic methods of taking acoustic fingerprints of acoustic sounds and comparison methods to detect changes in such fingerprints-such as by spectral subtraction. It is noted that a wide variety of such means would be useful to the practice of the present invention.

The three following additional special cases are also included within the scope of the present invention:

1. One may choose to permanently mount a therapy transducer adjacent to, upon, or physically within the implant (not shown). For example, the valve body 2 or leaflets 3A, 3B of the Figure could include an embedded or co-laminated miniature ultrasound transducer(s) that excites some or all of the valve structures or at least their surface deposits. This may be particularly doable if the transducing material is embedded and unexposed. Leads for electrical excitation of such a miniature transducer could be provided as necessary, as is known to the pacemaker art, for example.

2. A functioning valve (or non-functioning stuck valve) may be held in place for a few heartbeats or more in order to access deposits which are otherwise hard to get to with a sufficient acoustic exposure. An exemplary case would be that wherein acoustic device 7 of the Figure is covered by a saline-filled balloon (not shown) and the balloon is pushed into or placed into the valve to hold it open in a damage-free manner while it is inspected, fingerprinted and/or treated for deposit removal. The transducer would deliver its acoustics through the saline from a standoff distance, for example. One could also envelop the transducer in a balloon and insert the balloon/transducer into the valve if not through it to operate on the inside and/or far side of the valve.

3. The transducer or acoustic emitter of the invention may comprise a magnetostrictive transducer of the type widely known to the art. A key advantage of such transducers is that the excitation field that excites the magnetostrictive material may optionally be remote from the excited material (the emitting implant component to be cleaned for example). Thus, one could have a magnetic or electromagnetic varying field applied to the body non-invasively, yet still have the implanted prosthetic be excited acoustically via this magnetostrictive mechanism. This could thus be done without any tissue-penetrating leads.

It is emphasized that in the Figure, catheter item 7 is shown as being a forward-firing or emitting transducer. One may also utilize a side-firing transducer or radial-firing transducer, particularly if it is to be passed into the valve body as just mentioned, for example. For the purposes of the invention, an emitter emits acoustics regardless of whether the acoustics are themselves generated by the emitter, as they would be for a transducer-emitter, but as they would not be if the emitter were simply an output port of an acoustic waveguide connected to a remote transducer pumping acoustics into the connecting waveguide. By "acoustic emissions" we mean at least one of compression, rare-faction or shear waves which travel at or near a speed of sound of a material. These may be single-pulse, multipulse, pulse-trains, bipolar pulses, unipolar pulses, symmetric pulses, asymmetric pulses, inaudible vibrations or audible vibrations. They may have amplitudes in the general range of a micron or so up to a fraction of a centimeter per the recommended frequency limits. The highest frequencies described have the smallest wavelengths. Variable frequencies and therefore variable wavelengths may be employed as is known for broadband or multitone emitters. These are a good choice to help avoid exciting a resonance that is within the scanned frequency range.

Along the lines of item 2 above, included within the scope of the invention are transducers or emitters that are mounted in or held by surgical tools, clamps, balloons or other manipulators that aid the surgeon. Such manipulators may, for example, include all manner of access scopes, laparoscopes, gastro-scopes, catheters, cannulas, handheld tools, mechanical clamps, suction-based clamps or robotic grippers. Balloons or any other soft standoff or appendage may be interspersed between the acoustic probe 7 and any portion of the implant, member or organ and pass emissions to or from the implant, member or organ in a manner to avoid damage or scratching the implant, member or organ. The balloon, standoff or appendage may be utilized to aid in the temporary clamping or holding of the moving part of the implant, member or organ such that at least one deposit can be better accessed.

It will be clear to the reader now that one might further incorporate additional features along with the transducer(s) or acoustic emitters. One such feature could be a suction or flushing means or a trapping means to either suck out removed debris or to catch it in a filter or net at, near or away from the implant being cleaned, either during therapy and/or after the therapy. Such trash-collection features are known for clot-busters used in lumens and for carotid artery and cardiac installation. Another feature could be a modification to the implant's geometry or to its material makeup to make it easier to deliver the inventive therapy or make it easier for the acoustics to pass into certain regions of the targeted implant. For example, one might provide a mating feature on the implant such that a portion of the therapy emitter aligns favorably to illuminate or excite pre-selected portions of the implant prone to deposition. As another example, silicone or other polymer might be used to at least coat portions of the implant such that emitted acoustics are favorably absorbed causing at least one of localized heating and localized flexure of the surfaces supporting the deposits. It should be noted that direct and indirect resonation can provide very appreciable surface deformations to a flexible silicone coating (or component) that can knock off or shed deposits. One might also release the taught drugs locally at the implant as through a catheter. The present inventors stress that although the discussion herein has focused on heart valves as an exemplary example, also included in the scope of the invention are lumen-based natural and artificial valves, such as those found in the venous systems of the legs. Other candidate implants would include ports or other access devices wherein the moving part is yet another device, lead or catheter which must be passed into or through the port or access device on at least one occasion or at least once after a deposit may have formed. What all of these have in common is that deposits may interfere with a mechanical operation or function necessary for the implant to serve its function.

The foregoing discussion has been primarily directed to the removal of deposits around or upon moving parts of valves or implants. Other types of deposits known to cause valve problems are blood-borne bacteria, or even fungus, which frequently take up residence at or in natural or prosthetic valves. Such bacteria may get into the blood from a simple skin cut or from a dental procedure for example. Untreated, these bacteria can destroy the valve or at least cause blood-leakage at the edges of the valve. Prosthetic valves and compromised natural valves are particularly prone to such infectious damage. This valve infection is called endocarditis. The blood leakage is endocarditis-caused leakage. Included within the scope of the invention is the acoustic treatment of endocarditis tissues in or around natural or prosthetic heart valves. This treatment of infection or leakage-damage caused by deposited bacteria may comprise one of two types. The first type is outright killing of the bacteria by acoustic energy exposure or by the heat generated by such an exposure. The acoustic emissions may be directed, at least in part, to a prosthetic valve component, whereby acoustic heating of the component causes heat to be conducted into adjacent endocarditis-laden tissue, thereby at least partially killing the endocarditis bacterial or fungus. A catheter or other lumen-delivered device may, for example, be used to deliver the acoustic emissions.

The second type is sealing of blood leakage at the bacteria-caused leaks, such as by heat-induced blood clotting to plug such leaks. Such acoustic emissions may serve as a therapy for endocarditis. In all cases, the bacterial deposit is attacked and at least partly killed and thus is in keeping with the teaching herein of removing or reducing undesired depositions. Consistent with the other teachings herein, one may utilize an antibacterial or other helpful drug with the ultrasound exposure delivered to the valve or implant in any manner. Such a drug might be delivered locally to the infected valve via the aforementioned optional inflated balloon covering the emitter. The previously mentioned ranges or acoustic power and frequency are also applicable-particularly the higher powers and frequencies.

The therapy treatment may require only one therapy session. Alternatively, two or more therapy sessions may be conducted at different times or on different days.

The reader will readily appreciate that the inventive therapeutic acoustic emitters and/or fingerprinting apparatus can optionally be cointegrated with an ultrasonic imaging probe such that two or more of visualization, fingerprinting, and therapy can be delivered by one tool.

What is claimed is:

1. Invasive or minimally invasive apparatus for removal, breakdown or erosion of undesirable deposits present on, at or in actuating bodily implants or actuating bodily-members or organs of a patient comprising:

at least one distal acoustic emitter capable of directing acoustic energy toward a target bearing said deposits for the purpose of removing at least some of said deposit and recovering a desired degree of actuation;

an exciter to power and control the emitters acoustic operation;

the distal emitter including a deformable or soft standoff, protective member or appendage, the standoff at least one of (i) preventing or inhibiting direct emitter-target contact, (ii) allowing for gentle stoppage or suppression of the targets actuation for deposit removal, and (iii) allowing for passage of the emitter into or through the actuator without damaging the actuator, wherein the standoff comprises a saline filled balloon;

a proximally grippable scope, catheter, handle, guidewire, sheath or a gripping robot distally supporting the emitter and allowing a practitioner to control acoustic coupling of and use of the emitter on the target;

wherein by actuating is specifically meant that the implant or body member being treated for deposit has (a) adjacent, joined or mating portions which normally at least one of swing, hinge, pivot, distend, or flex relative to each other at least once or (b) mating parts which are plugged, connected, threaded or passed into or through each other at least once; and said deposit either currently negatively impacts normal actuation or threatens to worsen such that it eventually degrades actuation, thereby negatively impacting the patient.

2. The apparatus of claim 1 wherein said actuation comprises any one or more of:
desirable swinging, pivoting, hinging or occluding;
desirable plugging, unplugging, threading or connecting; or
desirable flexing or distending.

3. The apparatus of claim 1 wherein the implant or member is a cardiac, arterial or lymphatic valve of any natural, prosthetic or implanted type or is an implanted connector of any type.

4. The apparatus of claim 1 wherein a drug or chemical agent is employed at any time to aid in the acoustic removal of the deposit material in any manner.

5. The apparatus of claim 1 wherein the acoustic power employed is sufficient to cause at least one of blood streaming, blood or deposit cavitation, deposit erosion or deposit-heating useful in said removal.

6. The apparatus of claim 1 wherein acoustic power is being delivered continuously or in a pulsed manner, either gated or not gated to the heartbeat.

7. The apparatus of claim 1 wherein either or both of imaging guidance or acoustic signatures are employed to any of plan, assess, guide, gate or monitor a removal task.

8. The apparatus of claim 7 where said imaging or acoustic signatures specifically monitor an aspect of actuation state or performance.

9. The apparatus of claim 7 wherein the specific location of preexisting deposits on or at an actuator is known via said imaging or signature and targeted meaning the fouled portion of the actuator is specifically preferentially targeted.

10. The apparatus of claim 7 wherein the imaging or signature acquisition means is integrated with or proximal to the emitter.

11. The apparatus of claim 1 wherein any one of the following is employed:
a cavitation enhancing agent, including microbubbles;
a physical trap or drain to safely catch or route deposit debris after removal.

12. The apparatus of claim 1 wherein a deposit includes one or more of:
pannus, bacteria, endocarditis related growths, calcium containing deposits, fat containing deposits, fungus, plaque, fibrous containing deposits, thrombus, clot related materials, any flow-restricting deposits or biofilms.

13. The apparatus of claim 1 wherein the actuation occurs between one or more of:
two or more portions of one or more natural body parts;
two or more portions of one or more implants regardless of whether the implant(s) is constituted of tissue or engineering materials; or
a natural body part and an implant part.

* * * * *